(12) United States Patent
Thomas et al.

(10) Patent No.: US 10,258,500 B2
(45) Date of Patent: Apr. 16, 2019

(54) LIFE CRADLE DEVICE FOR INDUCING NEONATAL HYPOTHERMIA

(71) Applicant: PLUSS POLYMERS PVT. LIMITED, New Delhi (IN)

(72) Inventors: Niranjan Thomas, Vellore (IN); Nishit Soni, Orai (IN); Suman Kumari, Guwahati (IN); Apoova Balwani, Thane (IN); Devendra Jain, New Delhi (IN)

(73) Assignee: PLUSS ADVANCED TECHNOLOGIES PVT. LTD., Gurgaon (IN)

( * ) Notice: Subject to any disclaimer, the term of this patent is extended or adjusted under 35 U.S.C. 154(b) by 761 days.

(21) Appl. No.: 14/779,965

(22) PCT Filed: Jun. 17, 2014

(86) PCT No.: PCT/IN2014/000400
§ 371 (c)(1),
(2) Date: Sep. 24, 2015

(87) PCT Pub. No.: WO2014/203274
PCT Pub. Date: Dec. 24, 2014

(65) Prior Publication Data
US 2016/0051403 A1    Feb. 25, 2016

(30) Foreign Application Priority Data

Jun. 18, 2013  (IN) .......................... 1796/DEL/2013

(51) Int. Cl.
*A61F 7/02*    (2006.01)
*A61G 11/00*   (2006.01)
*A61F 7/00*    (2006.01)

(52) U.S. Cl.
CPC .............. *A61F 7/02* (2013.01); *A61F 7/0053* (2013.01); *A61G 11/00* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 8,257,417 B2 | 9/2012 | Chen et al. | |
| 2010/0010599 A1* | 1/2010 | Chen ........................ | A61F 7/02 607/112 |
| 2012/0330388 A1 | 12/2012 | Chen et al. | |

FOREIGN PATENT DOCUMENTS

| | | |
|---|---|---|
| CN | 102105119 A | 6/2011 |
| DE | 4425306 C1 | 2/1996 |
| EP | 2276438 A1 | 1/2011 |

OTHER PUBLICATIONS

Studies on poly vinyl chloride/fatty acid blends as shape-stabilized phase change material for latent heat thermal energy storage; Department of Chemistry, Gaziosmanpasa University, 60240, Tokat, Turkey; Department of Chemistry Karadeniz Technical University, 61100, Trabzon, Turkey: vol. 13 (Ahmet Sarl & Kamil Kaygusuz) Jun. 2006, whole document.

* cited by examiner

*Primary Examiner* — Joseph A Stoklosa
*Assistant Examiner* — Adam Avigan
(74) *Attorney, Agent, or Firm* — Helix Patent Services LLC

(57) ABSTRACT

The present invention relates to a life cradle device for the purpose of inducing therapeutic hypothermia in neonates suffering from birth asphyxia. The device essentially consists of a rigid outer skeleton which could be fitted with removable mattresses containing form stable organic phase
(Continued)

change materials effecting instant and sustained cooling. Multiple compartments of different phase change material composition functional at different temperatures are arranged in layers to replicate cooling performances as in conventional cascading systems. The device is also designed to have thermo-chromic indicators with an option of probes for automation control techniques. The device may also be fitted with thermostat controlled infant radiant warmer to automatically switch on when the infant is cooled down below requirement as a safety consideration.

15 Claims, 2 Drawing Sheets

(52) U.S. Cl.
CPC ............... *A61F 2007/0086* (2013.01); *A61F 2007/0088* (2013.01); *A61F 2007/0093* (2013.01); *A61F 2007/0095* (2013.01); *A61F 2007/0204* (2013.01); *A61F 2007/0219* (2013.01); *A61F 2007/0292* (2013.01); *A61G 2210/70* (2013.01)

LIFE CRADLE DEVICE FOR INDUCING NEONATAL HYPOTHERMIA

FIELD OF THE INVENTION

The present invention discloses a new and economical method of instant as well as sustained cooling of neonates (new born babies) that suffer from birth asphyxia using multilayer form stable phase change material based device to effect neonatal therapeutic hibernation.

BACKGROUND OF THE INVENTION

Hypothermia is a highly effective treatment when applied to neonates suffering from birth asphyxia. Research reveals that damages following asphyxia can be curbed effectively by lowering the infant's body enough to induce a state of transient hibernation. Meta-analysis of a large number of randomized controlled trials show that hypothermia for 72 hours started within 6 hours of birth significantly increased the chance of survival circumventing brain damage. Incidences of neonatal encephalopathy occur at a frequency of up to 20 per 1000 births in developing nations. Thus there is a need to develop technologies to prevent neonatal asphyxia and complications that arise from it.

Treatment mandates a strict temperature control in the bandwidth of 33 to 34° C.

Indian patent application no. 23/2/DELPN/2005, discloses an apparatus for cooling a patient to a temperature below normal body temperature using an air cooling system which is of high cost.

Many inventors have proposed the use of phase change material composites to effect cooling.

Basically Phase change materials (pcms) store thermal energy in the form of latent heat and depending on the material used they can be exploited for thermal regulation in the required temperature range.

US patent application no. 2012/0330388 describes the thermal regulation system comprising conventional PCMs. However the solid pcms used in the invention are very hard to touch causing discomfort to the neonate and further the system is not leak proof thus making it unsuitable for neonatal use.

PCT Application number WO03061412 A3 relates to garments for heating or cooling a body part of a wearer of the garment. The cooling or heating layer comprises a flexible substrate having disposed thereon a two dimensional array of pockets containing phase changing material. But the invention focuses on garments in which can be stored bladders containing a phase change material, not an assembly for the effective cooling of neonates.

U.S. Pat. No. 8,257,417 B2 discloses a system comprising a temperature regulation element and a bedding element that includes a phase change material which changes between a liquid phase and a solid phase. However patent does not claim cooling and PCMs employed are not suitable in the effective temperature range.

U.S. Pat. No. 6,004,662 A discloses a PCM composite using multiple PCM's with different transition temperatures randomly distributed throughout the composite. It however, does not disclose a system to regulate the cooling of the bedding element and phase change materials enclosed in different compartments that are used in conjugation with an enclosure to form neonatal cooling device. It also does not specify PCM compositions effecting cooling and sustaining temperature in the range of 33 to 34° C.

It is thus an object of the invention to provide a device which can effect instant and sustained cooling of neonates in the temperature range of 33 to 34° C.

It is another object of the invention to use multiple sheets of reinforced form stable fatty acid and fatty acid ester based pcms functional at different temperatures to give a temperature gradient as in a cascaded system to effect and maintain hypothermia.

It is yet another object of the invention to have a portable and low cost model that is thermally conductive, leak proof, skin friendly and provided extended cooling without a requirement for continuous or frequent recharging so that device could be effectively used even in rural areas which do not have access to state of the art neonatal facilities.

DESCRIPTION OF INVENTION

The present Invention discloses a unique neonatal device that consists of a rigid thermostable skeleton enclosing removable temperature regulation elements consisting of FSPCM (form stable phase change material). The phase change material has a property which changes between a liquid phase and a solid phase within the desired temperature range. Phase change material compositions functional at different temperatures are enclosed in polymeric mattresses arranged in layers to replicate cooling performances as in conventional cascading systems.

Figure 1:
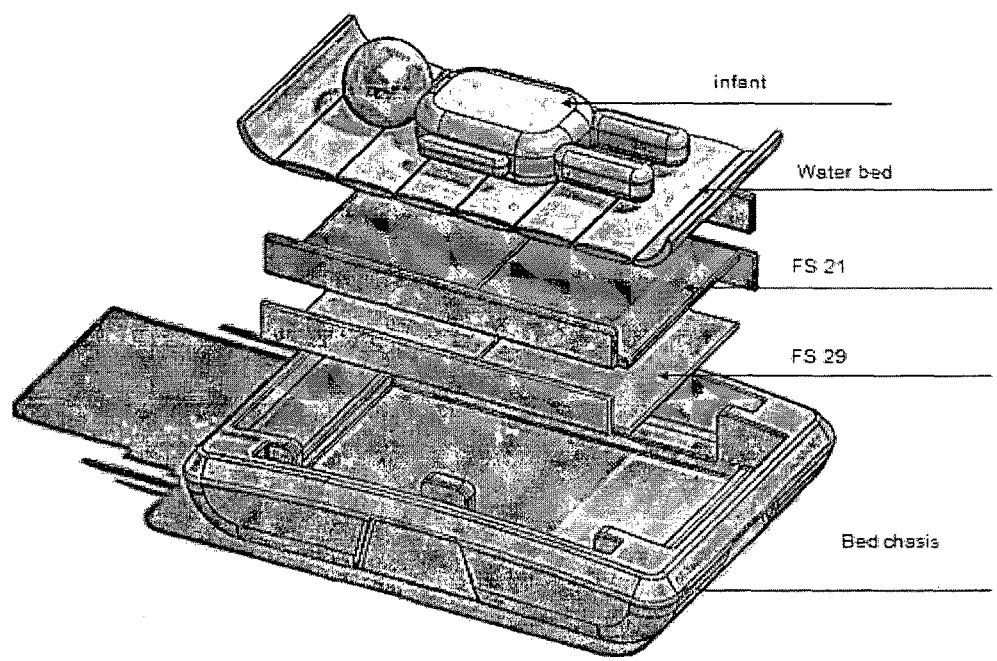
FIG. 1 illustrates a perspective view of a neonatal hypothermia inductive device.

There are five crucial components in the device (FIG. 1), namely;

i. Rigid thermostable skeleton that could be either fitted to a basinet or function independently as a cot housing hereby referred to as Bed Chasis.

ii. One or more polymeric mattress(es) containing polymer blended reinforced organic fatty acid based PCM placed inside the thermoplastic skeleton hereby referred to as FS 29 mattress iii. One or more polymeric mattress(es) containing polymer blended reinforced organic fatty acid ester based PCM hereby referred to as FS 21 mattress placed above FS 29 mattress to establish direct contact with neonate or below the water bed iv. Thermochromic indicators placed on surface of the FS 29 and FS 21 mattresses to ensure maintenance of required temperature limits v. A water bed or a gel bed on which the infant is placed vi. Optionally a thermostat controlled infant radiant warmer to automatically switch on when the infant is cooled down below requirement as a safety consideration.

Construction and Function of Crucial Components

Rigid Thermostable Skeleton:

The Rigid thermoplastic skeleton is made of rotomolded medical grade HDPE/PP with a gloss finish and no sharp nooks or corners for enhanced safety and easy, hygienic cleaning. Food grade colour additives are used for aesthetic value and the skeleton is filled inside with injected PUF foam. It basically functions to provide thermal insulation (for longer performance), rigidity and handlability of overall system. Thickness could be variable depending on thermal insulation requirements derived from theoretical calculations made for the heat rejection dynamics between the infant and the pcm beds in an ambient temperature range between 35-45° C. However, it has a minimum insulation thickness of 3 cm.

FS 29 Mattress:

The FS 29 mattress is basically an FS 29 formulation suitably encapsulated in polymeric films. The mattress contains an FS 29 formulation suitably encapsulated in polymeric films further bearing aluminium tape on top surface of mattress for equal and uniform distribution of heat fluxes. The FS 29 formulation comprises a mixture of SEBS polymer blended with a eutectic organic PCM mixture of capric acid and stearic acid with expanded graphite for enhanced thermal conductivity. Organic fatty acid based pcms are chosen primarily to replicate the heat transfers through the infant's skin which is predominantly made of fatty acid derivatives. Further we wish to avoid cooling and heating extremes caused by salt hydrate based pcm. Chosen pcms can be form stabilized, which improve handlability and performance stability. FSPCM is made by blending polymer with PCM.

The main function is to sustain infant temperatures at 33-34° C. for as long as possible in the due course of 72 hours of treatment.

In one of the embodiments of the invention the FS 29 formulation comprises SEBS polymer (10%), eutectic pcm mixture (80%) with capric acid (86%) and stearic acid (14%) expanded graphite (10%) encapsulated in nylon PE multilayer or PU films. It further has a phase change temperature in the range of 27 to 30° C., Latent heat capacity in the range of 140-160 KJ/kg, Thermal conductivity in the range of 0.4 to 0.9 W/m·K and Density in the range of 800 to 1000kg/cu·m.

Aluminium tape is applied on the top surface of the mattress for equal and uniform distribution of heat fluxes.

In another embodiment, the slabs are prepared with hollow coils running through them and coming out from the sides. These coils are then connected to refrigeration coils so that cool media can run through the PCM slabs, efficiently charging them.

Thermo-chromic indicators are also placed on the top surface of the mattress. These are used to judge whether a PCM block is fit for use for infant cooling or not. (Indication of surface temperatures between 20 and 30 C. renders mattress fit for use)

In yet another embodiment thermocouple probes are inserted to indicate temperatures, or to initiate any sort of automation control (such as caution alarms).

In yet another embodiment for the sake of convenience, these mattresses are broken down into smaller slabs and assembled in the cavity to form a continuity of FS-29.

FS 21 Mattress:

The FS 21 mattress is basically an FS 21 formulation suitably encapsulated in polymeric films.

In one of the embodiments the formulation has SEBS copolymer (10%), graphite (10%), n-butyl stearate (80%).

In another embodiment FS 21 formulation contains SEBS (10%), graphite (10%), eutectic mixture (80%) comprising Capric acid (75%) and myristic acid (25%) encapsulated in nylon PE multilayer or PU films.

The thickness and number of FS 21 mattresses are adjusted to effect quick and safe cooling of infant to 33° C. after which it functions as a flux conducting layer.

In a preferred embodiment the FS 21 formulation has a Phase change temperature in the range of 18-21° C., Latent heat capacity in the range of 110-115 KJ/kg, Thermal conductivity in the range of 0.3 to 0.9 W/m·K, and Density in the range of 800 to 1000 kg/cu·m.

The pouching and encapsulation, including a layer for uniform dissipation, as well as thermo chromic indicators, is same as FS 29 mattress. This mattress can also be broken down into smaller halves for the sake of convenience and storage.

Water/Gel Bed

In one of the embodiments the water bed comprises segmented pouches of soft embossed polyurethane, surlyn or nylon multilayer puffed with a mixture of 80% iso-propyl alcohol and 20% demineralized water. The pouches are segmented to ensure that they remain puffed with water and support the infant's body weight.

In yet another embodiment the water bed contains demineralised water with suitable antimicrobials.

In yet another embodiment, the water is first mixed with thermally conducting fillers, and then gelled/thickened, to form a conductive gel bed. The fillers used may be particulate or strand-like and must have a thermal conductivity of at least 5 W/m·K. These may be derived from aluminium nitride, boron nitride, copper particles or strands, aluminium particles or strands, natural graphite, flake graphite, intercalated graphite, or any other variety of treated particulate thermal conductors. The gelling may be done with suitable thickeners such as gelatin, starches, low molecular weight polyols, etc. or with commercially available superabsorbent polymers. Its basic function is to provide comfortable resting surface for the infant as well as good thermal performance of the device by absorbing the heat from the infant and transferring it efficiently.

A preferred embodiment bears outer dimensions of 54 cm×18 cm. Usually 5 segments are made in the pouch of the dimensions 1.2 cm×18 cm.

The device provides a "quasi-servo" temperature control method that is designed to regulate body temperature and can be subjected to semi automation techniques for treatment of birth asphyxia. The device does not require a continuous backup. It is designed to be used in remote areas lacking consistent power facilities or for transport based cooling in ambulances that helps to save diesel and generator costs. The setup is simple and the design of the life cradle is made to be able to function easy and clean to handle. The maintenance costs of the device are very low so that it is affordable where incubators are not installed.

The components are easily separable, easy to clean and can be replaced. The technology is non-invasive, hence very easy and safe to operate.

The device can be operated on a manual basis and also be converted for a semi-automated operation. The device requires a lower supervision and could be operated with little manual instructions also.

The cradle maintains the optimum temperature of the assembly so efficient so as to lower shivering of the infant when placed in it or cause negligible shivering as compared to convective or ice cooling.

Thermo-chromic indicators are also placed on the top surface of the mattress. These are used to judge whether a PCM block is fit for use for infant cooling or not. (indication of surface temperatures between 20 and 30 C renders mattress fit for use)

Alternately, thermocouple probes may also be inserted to indicate temperatures, or to initiate any sort of automation control.

Thermochromic Indicators and Probes:

Thermochromic indicators are strips of paper with thermo-responsive pigments incorporated in them, preferably thermochromatic liquid crystals of temperature ranges 10 to 40 C., and more preferably, thermochromatic liquid crystals of temperature ranges 20 to 30 C. By their inherent property of changing colour at a specific temperature, these thermochromatic liquid crystals form a suitably accurate temperature indication system that is easy to understand and flexible in use. In an illustration, a thermochromic indicator strip, with temperature range from 12 C. to 32 C. is placed on a slab at 21 C. Soon after, the marking "21" on the strip turns green, while marking "20" on its left turns blue and "22" on its right turns red, indicating the correct temperature of the surface.

Apart from aiding the user in knowing when the PCM slab may have discharged, a more important use of these indicators is when PCM slabs are charged by storage in refrigerators. In such cases, the slabs reach very low temperatures and require a slight pre-warming before these can be safely used in contact with the infant. Thermochromic indicators may thus be suitable in indicating the readiness of PCM slabs for use in the device. Said indicators are chosen from a selection of commercially available brands, such as LCR Hallcrest, Tip temp, Dwyer Inst, Siltech, Veritech, etc., and LCR Hallcrest and Tip Temp are more preferred brands.

Often times, these indicators may be replaced with conventional thermal probes. These may preferably be resistance thermometers, which can accurately indicate the temperature of the mattress at any given incident. These are more preferable when portability may be compromised. Further, for analysis of skin or core body temperatures of the infant, only apt thermal probes are to be used.

Thermostat Controlled Infant Radiant Warmer:

As described, present invention has an excellent control over infant's core body temperatures, and maintains it in the strict regimen of 33-34 C. even though it is a passive system with virtually no moving parts at all.

However, even so, the basic essential device has limitations in that if the body mass index of the infant under cooling is very low, there are chances of over-cooling the baby. As such, manual supervision and undertaking becomes necessary.

However, in an alternate setup, a thermostat controlled infant radiant warmer may be used in combination with the essential system. This system may be switched on whenever the infant's temperatures tend to drop undesirably, and may be switched off when the temperatures stabilize.

Alternatively, said thermostat controlled infant radiant warmer may be automated, where based on temperature feedback from the rectal probe attached to the infant, the warmer may switch on or off desirably.

Further, such a radiant warmer may use servo-mechanism for said control.

Further, the modified radiant warmer in such a setting is programed to not warm at more than 40%, and more preferably not more than 20% of total radiation power of the lamp. Such a warmer also has a dual set-point, and activates when core-body temperature drops below 33.4 C., more preferably below 33.2 C.; and deactivates when the temperature climbs back to 33.6 C., or more preferably, above 33.8 C.

Further, the modified radiant warmer is to be accompanied with a hard alarm system, which shall sound every time temperature drops below 33.3 C, or more preferably below 33.1 C., or climbs over 33.7 C., more preferably over 33.9 C.

It is understood that the combination of a servo-controlled warmer with the PCM based device is not only novel, but still more economical as compared to servo-based cooling systems prevalent in the market, currently.

Layout and Assembly of Device

The components are shaped in a way to fit one into other and all crucial components are required for a complete working of the device.

Step 1: The rigid thermostable skeleton is cleaned and placed in an infant warmer basinet or any such suitable place Step 2: FS 29 mattress (hitherto being charged) is removed from charging and placed inside the chasis as one would place mattress on a cot/bed Step 3: FS 21 is similarly removed from charging and placed on top of FS 29 mattress.

Step 4: The water bed is placed on top of FS 21 mat and the system is allowed to stay like this for a few minutes.

Step 5: The infant to be treated is placed into this assembly on top of the water bed.

Additional step: If provided for, the ancillary radiant warmers which are modified for the specific use are to be used as per the pre-existing medical protocols.

Charging and Discharging Attributes

The overall functioning of the device is dependent primarily upon the phase change process of the FS 29 and the FS 21 mattresses. The mattresses essentially function as thermal reservoirs, and just like a battery (electrical charge reservoirs), these require "charging" before they are fit for use, and "discharge" towards the end of their use. A mattress is completely discharged, when it may no longer be able to hold the temperature of the proposed system at desired levels, as it is no longer able to absorb heat by the virtue of its latent heat capacity.

Charging essentially involves bringing the temperature of the mattresses below their phase change temperatures, such that they regain their ability to absorb large quantities of heat in latent form. As such, the mattresses are designed for an easy and rugged charging atmosphere, and can be charged by simply subjecting them to temperatures below 24 C. (for FS 29) and 16 C. (for FS 21). Thus, in one embodiment, it is suggested to charge the FSPCM mattresses by placing them in common household refrigeration systems.

By its inherent scope, the device is expected to be very applicable in hospital ICUs, which are usually air conditioned. Thus, in an alternate embodiment, the charging of FS 29 is suggested to be facilitated by the cool, conditioned air of the ICUs, provided said unit is set at an ambient temperature of or below 25 C.

In an alternate embodiment associated with the FS 29 mattress properties, the mattress comprises of hollow tubes, which can be connected to refrigeration tubes, such that refrigerants at low temperatures may be carried through the PCM mattress to charge it efficiently. Refrigerant temperatures can range from 0 C. to 24 C., and more preferably from 10 C. to 16 C. These may include common, and commercially available heat transfer oils and brines such as calcium chloride brine, sodium chloride brine, alcohol, water, glycols, alcohols, air, and similar non-freezing solutions in the given temperature range.

In a further embodiment, FS 21 mattress may then be charged by simply placing them over the FS 29 mattress being charged as aforementioned.

In a further embodiment, the refrigerant passing through the PCM mattresses for charging purposes may be cooled via compressors, air conditioning units, evaporative coolers, "pot-in-pot" systems or such other economically viable systems available in prior art.

In yet another embodiment, the FSPCMs may be cooled by systematic evaporation of solutions that can form liquefiable vapors upon contact and consequent absorption of heat from the surface of the mattresses.

In yet another embodiment, the mattresses can be charged through contact cooling by subjecting them to colder surfaces which are maintained at temperatures as described above.

Finally, in a derived embodiment, the mattresses may be charged in a "pot-in-pot" system, wherein the mattresses are placed in an empty, conducting inner pot, which is further suspended in a fluid containing outer, clay pot. The fluid is cooled by either evaporative cooling on the surface of the outer clay pot or by dissolution of solutes which have an endothermic heat of dissolution in said fluid. This cooled fluid in turn cools the inner, conductive pot, initiating contact cooling as described above.

Functioning Attributes of the Device

As mentioned earlier, the predominant object of the device is to exploit the latent heat property of the FSPCM mattresses in order to efficiently function as a neonatal cooling device.

The precise requirements of sustaining the temperature of the suffering neonate between 33 and 34 C., have been mentioned as the highlighting challenge previously. However, an equally challenging proposition is to first bring down the temperature of the neonate from 37 C. to 33 C. as soon as possible; this is a challenge because in dealing with the sensitivities of an infant's biology, most established methods have been risky, and it is essentially because of this reason that servo-mechanism based coolers have been the popular option in the treatment (servo-mechanistic devices have the capability to adjust the cooling rates as per the difference between target temperatures and persisting temperatures). To illustrate, the following scenarios may be considered:

1. The infant is cooled slowly: the longer it takes for the neonate to come to 33-34 C., the higher are its chances of sustaining brain tissue injuries
2. The infant is cooled rapidly: In every such scenario, there would be a requirement of manual experience and supervision; even so, the infant runs the risk of getting overcooled due to late cut-off of high-speed cooling (the device might be switched off when temperatures are reached, but the inertia may be enough to pull the infant's temperature further). Even if overcooling is avoided, in case rapid cooling takes place via conduction, due to the human body's slow thermal dissipation, there is a high risk of localized overcooling. This is more harmful, as a timely detection of localized cooling is more difficult than whole-body overcooling.

There exists, however a third scenario, where the infant may be rapidly cooled up until a certain time period, after which the cooling flux is modified to a much slower level. This is how servo-mechanism functions. However, the present invention claims to have engineered a multi-PCM system that can replicate the same effect without any servo-mechanism. Essentially FS 21 is chosen for its phase change at a lower phase change temperature of 18-21 C. At its phase change temperature, the thermal gradient between an uncooled infant and FS 21 can be as high as 19 C.

As per Fourier's law, the rate of heat transfers will be conveniently high to quickly pull down the neonate's temperatures. At the same time, due to the fact that the gradient is no higher, and that the materials used in the mattress are similar to skin and fat layers of an infant in terms of thermal properties, chances of localized overcooling are severely reduced. The thickness of the mattress is so designed, that in the time estimated to pull down the infant's temperature from 37 C. to 33 C., the mattress conveniently discharges, and the gradient is decreased.

After the discharge of FS 21 mattress, the FS 29 mattress with a phase change temperature of 27-30 C. comes in play. In this step, the thermal gradient is reduced to around 3-4 C., and the heat rejection and absorption rates are conveniently matched to bring the temperature of the infant in steady state. As a result, the core body temperatures are sustained in the infant between 33 C. and 34 C. for as long as the FS 29 mattress can absorb energy by the virtue of its latent heat capacity.

EXAMPLES

Given below are some examples to elucidate the actual working of the device as established from clinical trial.

In given examples, the following terminologies are to be used, as explained.

a. Temperature drop: Infant's temperature as pulled down from 37° C. to 33° C.
b. Sustenance: The act of maintaining infant's temperature between 33 and 34° C.
c. Overshoot: Instances of infant's temperature crossing over 34° C.
d. Overcooling: Instances of infant's temperature falling below 33° C.

Example 1

The device was assembled as per the steps mentioned in "Layout & Assembly of device". A layer of charged FS 29 mattress with a thickness of 2.5 cm and FS 21 mattress with a thickness of 7 mm each were used. On the top, a water bed of thickness, 1 cm was also used. The weight of the infant was 2000 gms. The temperature drop took 20 minutes, and the sustenance from the FS 29 layer lasted for 24 hours. After this, the FS 29 layer needed to be replaced with another charged mattress. There were no instances of overshooting or overcooling. The thermochromic indicator indicated temperature change of surface temperature as between 23 and 31 C. for the FS 29 mattress, and predominantly stayed at 28-29 C. range.

Example 2

The device was assembled in the same manner as given in example 1 except that there was no water bed employed in this case. The weight of the infant was 2200 gms. The performance of the device were similar to Example 1, however, there were more fluctuations in the core body temperatures of the infant between 33 to 34 C. as compared to the previous example. The thermochromic indicator performed same as before and the mattresses were considered discharged when indicator shows temperature of 31 C.

Example 3

The device was assembled as per the steps mentioned in "Layout & Assembly of device" with the use of two layers each of FS 21 and FS 29 each. The infant weight was 2500 gms. The temperature drop takes 15 minutes, followed by requirement of warming using the radiant warmer for 24 minutes. Sustenance lasted for 29 hours, when both layers of FS 29 were replaced. No other instances of overcooling/overshooting were reported.

Example 4

The device was assembled as per the steps mentioned in "Layout & Assembly of device" with the use of three layers of FS 21, and one layer of FS 29. The FS 21 layer thickness was reduced to 5 mm, and FS 29 layer thickness was increased to 3.5 cm. The infant weight was 2300 gms. The temperature drop took 10 minutes after which it automatically stabilized at 33 C for 32 hours without replacement. No overshooting or overcooling was detected.

Example 5

Figure 2:
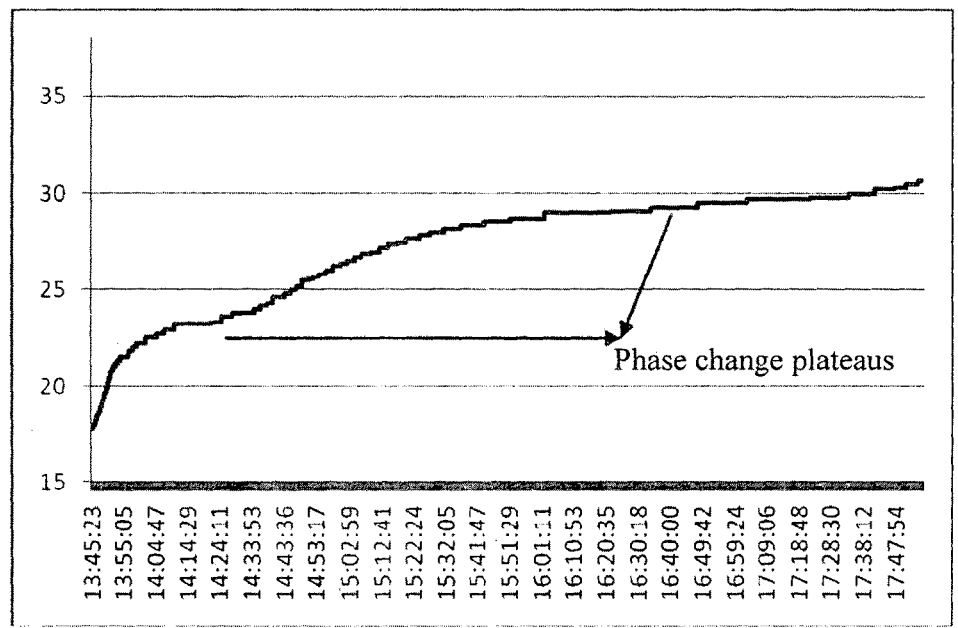
FIG. 2 illustrates a graphical representation denoting two phase change plateaus occurring between FS 21 mattress and the water bed during the ongoing treatment process, wherein the graph is plotted betwixt "Time on X-axis and Temperature on Y-axis."

The device was assembled as per the steps mentioned in "Layout & Assembly of device" with the use of one layer of FS 21 and two layers of FS 29. Infant weight was 1500 gms. Temperature drop took 15 minutes, and the device sustained cooling at 33 C. for remainder of treatment time (72 hours). There were four instances of warming required, but overcooling was not detected. RTD probes were used to note PCM temperatures in lieu of indicator strips and on the whole showed similar performance as before. The probe on top of the water bed showed temperatures of 32.5-33 C. throughout the treatment process. The probe at the interface of FS 21 mattress and water bed showed a clear cascading effect, with two individual phase change plateaus, one at around 29 C. and another at around 21 C. (FIG. 2).

Example 6

The device was assembled in the same manner as given in example 1. Infant's weight was 1900 gms. The infant warmer, which was used in aforementioned examples for warming the baby manually, was set on servo mode and a rectal probe from the infant was attached to the control system. Higher setpoint was 33.8 C. and lower setpoint was 33.2 C. The modified servo system was set to control the warmer power to no more than 30% of the available power rating. The temperature drop was in 13 minutes, and the cooling effect was sustained for 26 hours. Zero manual intervention was reported. Thermochromic indicators predominantly showed temperature of 29 C. on FS 29 mattress surface.

Example 7

This was similar to example 5. The infant weight was 2200 gms. However, the water bed was replaced with conducting gel bed. The temperature drop took 15 minutes after which it automatically stabilized at 33 C. for 32 hours without replacement. Overshooting or overcooling was not witnessed. The gel bed was also deemed more convenient than the water bed.

Example 8

In comparison with discussed device, multiple cooling trials consisted of using a single layer of PCM instead of multiple temperature cascaded system. Further, this PCM was an inorganic composition and in order to pull down temperature from 37 C. to 33 C. in the beginning, ice packs were employed. There were multiple instances of overcooling as well as a few instances of overcooling in this method with most of the patients whose weights ranged from 1700-2600 gms. The instances of shivering were also increased in these trials as compared to our original device. It should be noted in this context that in comparison with prior studies, we have found decreased instances of infant shivering (witnessed only during the initial onset and temperature drop) in use of our invention as compared to other existing technologies, including servo-based cooling devices.

The aforementioned description shall not limit the scope of the invention but a person skilled in the art will recognize modifications and changes can be made to the preferred embodiments of the invention without departing from the scope of the invention defined in the following claims.

We claim:

1. A life cradle device effecting instant as well as sustained cooling for inducing therapeutic neonatal hypothermia comprising:
   i) a rigid thermoplastic skeleton configured to be either fitted to a basinet or function independently as a cot housing;
   ii) a bedding component comprising:
      a) a removable water bed or gel bed adapted to receive an infant thereupon;
      b) removable one or more polymeric mattress(es) containing polymer blended reinforced organic fatty acid based PCM, placed inside the rigid thermoplastic skeleton, referred to as one or more FS 29 mattress(es);
      c) removable one or more polymeric mattress(es) containing polymer blended reinforced organic fatty acid ester based PCM, referred to as one or more FS 21 mattress(es), placed above the FS 29 mattress(es) to establish direct contact with neonate or below the water bed;
      d) thermo-chromic indicators incorporated in FS 29 and FS 21 mattress(es), configured to show an upper threshold and a lower threshold of required temperature limits, wherein the lower threshold is 33° C.

2. The life cradle device as claimed in claim 1, wherein said thermoplastic skeleton comprises rotomolded medical grade HDPE/PP based hollow chassis with food grade color additives for aesthetic value filled inside with injected PUF foam or any foam with thermal conductivity of of less than 0.03 W/m·K.

3. The life cradle device as claimed in claim 1, comprising the water bed wherein said water bed comprises segmented pouches of soft embossed polyurethane, surlyn or nylon multilayer puffed with a mixture of 80% iso-propyl alcohol and 20% demineralized or demineralized water with suitable antimicrobials.

4. The life cradle device as claimed in claim 1, comprising the gel bed wherein said gel bed comprises a gel that is prepared from a process comprising steps of:
   a) mixing water with thermally conducting fillers selected from a group comprising particulate and strand-like fillers, with a thermal conductivity of at least 5 W/m·K derived from a group of aluminium nitride, boron nitride, copper particles or strands, aluminium particles or strands, natural graphite, flake graphite, intercalated graphite, or any other variety of treated particulate thermal conductors; and
   b) gelling the mixture with suitable thickeners selected from a group of gelatin, starches, low molecular weight polyols, and commercially available superabsorbent polymers to form a conductive gel bed.

5. The life cradle device as claimed in claim 1, wherein said one or more FS 29 mattress(es) include a FS 29 formulation comprising a mixture of SEBS polymer blended with a eutectic organic PCM mixture of capric acid and stearic acid with expanded graphite and said FS 29 formulation being encapsulated in polymeric films further bearing aluminium tape on top surface of said one or more FS 29 mattress(es).

6. The life cradle device as claimed in claim 5, wherein said FS 29 formulation comprises SEBS polymer (10% of the FS 29 formulation), eutectic PCM mixture (80% of the FS 29 formulation) with capric acid (86% of the eutectic PCM mixture) and stearic acid (14% of the eutectic PCM mixture), expanded graphite (10% of the FS 29 formulation), encapsulated in nylon PE multilayer or PU films.

7. The life cradle device as claimed in claim 5, wherein said FS 29 formulation has a Phase change temperature in the range of 27 to 30° C., Latent heat capacity in the range of 140-180 KJ/kg, Thermal conductivity in the range of 0.3 to 1.5 W/m·K and Density in the range of 800 to 1300 kg/cu·m.

8. The life cradle device as claimed in claim 1, wherein said one or more FS 29 mattress(es) include a FS 29 formulation comprising SEBS polymer (10% of the FS 29 formulation), eutectic PCM mixture (80% of the FS 29 formulation) with capric acid (86% of the eutectic PCM mixture) and stearic acid (14% of the eutectic PCM mixture), expanded graphite (10% of the FS 29 formulation) encapsulated in nylon PE multilayer or PU films.

9. The life cradle device as claimed in claim 8, wherein said FS 29 formulation has a Phase change temperature in the range of 27 to 30° C., Latent heat capacity in the range of 140-180 KJ/kg, Thermal conductivity in the range of 0.3 to 1.5 W/m·K and Density in the range of 800 to 1300 kg/cu·m.

10. The life cradle device as claimed in claim 1, wherein said one or more FS 29 mattresses include a FS 29 formulation having a Phase change temperature in the range of 27 to 30° C., Latent heat capacity in the range of 140-180 KJ/kg, Thermal conductivity in the range of 0.3 to 1.5 W/m·K and Density in the range of 800 to 1300 kg/cu·m.

11. The life cradle device as claimed in claim 1, wherein said one or more FS 21 mattress(es) include a FS 21 formulation having SEBS copolymer (10% of the FS 21 formulation), graphite (10% of the FS 21 formulation), n-butyl stearate (80% of the FS 21 formulation) or a FS 21 formulation having SEBS (10% of the FS 21 formulation), graphite (10% of the FS 21 formulation), eutectic mixture (80% of the FS 21 formulation) comprising Capric acid (75% of the eutectic mixture) and myristic acid (25% of the eutectic mixture), encapsulated in nylon PE multilayer or PU films.

12. The life cradle device as claimed in claim 11 wherein said FS 21 formulation has a Phase change temperature in the range of 18-21° C., Latent heat capacity in the range of 110-115 KJ/kg, Thermal conductivity in the range of 0.3 to 1 W/m·K, and Density in the range of 800 to 1300 kg/cu·m.

13. The life cradle device as claimed in claim 1, wherein said one or more FS 21 mattress(es) include a FS 21 formulation having Phase change temperature in the range of 18-21° C., Latent heat capacity in the range of 110-115 KJ/kg, Thermal conductivity in the range of 0.3 to 1 W/m·K, and Density in the range of 800 to 1300 kg/cu·m.

14. The life cradle device as claimed in claim 1, wherein the thermo-chromic indicators are adapted to assume different colors to indicate sustenance, overshoot and overcooling of the device for the claimed temperature range.

15. The life cradle device as claimed in claim 1, further comprising a thermostat controlled infant radiant warmer configured to automatically switch on in response to a core-body temperature of the input dropping below a predetermined set-point.

* * * * *